(12) United States Patent
Yoon et al.

(10) Patent No.: US 12,303,701 B2
(45) Date of Patent: May 20, 2025

(54) METHODS AND IMPLANTABLE MEDICAL SYSTEMS THAT IMPLEMENT EXPOSURE MODES OF THERAPY THAT ALLOW FOR CONTINUED OPERATION DURING EXPOSURE TO A MAGNETIC DISTURBANCE

(71) Applicant: MEDTRONIC, INC., Minneapolis, MN (US)

(72) Inventors: Hyun J. Yoon, Vadnais Heights, MN (US); Wade M. Demmer, Coon Rapids, MN (US); Matthew J. Hoffman, St. Paul, MN (US); Robert A. Betzold, Fridley, MN (US); Jonathan D. Edmonson, Blaine, MN (US); Michael L. Ellingson, St. Louis Park, MN (US); Ben W. Herberg, Andover, MN (US); Juliana E. Pronovici, New Hope, MN (US); James D. Reinke, Maple Grove, MN (US); Todd J. Sheldon, North Oaks, MN (US); Paul R. Solheim, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/227,552

(22) Filed: Jul. 28, 2023

(65) Prior Publication Data

US 2023/0364430 A1    Nov. 16, 2023

Related U.S. Application Data

(60) Continuation of application No. 17/234,746, filed on Apr. 19, 2021, now Pat. No. 11,724,111, which is a
(Continued)

(51) Int. Cl.
*A61N 1/37*     (2006.01)
*A61N 1/368*    (2006.01)
*A61N 1/39*     (2006.01)

(52) U.S. Cl.
CPC ......... *A61N 1/3718* (2013.01); *A61N 1/3931* (2013.01); *A61N 1/3684* (2013.01); *A61N 1/3688* (2013.01); *A61N 1/3956* (2013.01)

(58) Field of Classification Search
CPC .. A61N 1/3718; A61N 1/3931; A61N 1/3684; A61N 1/3688; A61N 1/3956
See application file for complete search history.

(56) References Cited

U.S. PATENT DOCUMENTS 5,174,289 A    12/1992  Cohen
5,722,998 A     3/1998  Prutchi et al.
(Continued)

FOREIGN PATENT DOCUMENTS

CN    106110503 A    11/2016
EP      1935450 A1    6/2008
WO   2010126935 A2   11/2010

OTHER PUBLICATIONS

Kloostermann, Dr. E. Martin, MRI Remote Control Study (ROCON) Remote Management of Cardiac Devices Undergoing MRI, received Jan. 26, 2016, 7 pgs.
(Continued)

*Primary Examiner* — Catherine M Voorhees
(74) *Attorney, Agent, or Firm* — Shumaker & Sieffert, P.A.

(57) ABSTRACT

Implantable medical systems enter an exposure mode of operation, either manually via a down linked programming instruction or by automatic detection by the implantable system of exposure to a magnetic disturbance. A controller then determines the appropriate exposure mode by considering various pieces of information including the device type
(Continued)

including whether the device has defibrillation capability, pre-exposure mode of therapy including which chambers have been paced, and pre-exposure cardiac activity that is either intrinsic or paced rates. Additional considerations may include determining whether a sensed rate during the exposure mode is physiologic or artificially produced by the magnetic disturbance. When the sensed rate is physiologic, then the controller uses the sensed rate to trigger pacing and otherwise uses asynchronous pacing at a fixed rate.

12 Claims, 5 Drawing Sheets

Related U.S. Application Data continuation of application No. 16/409,921, filed on May 13, 2019, now Pat. No. 10,981,010, which is a division of application No. 15/487,713, filed on Apr. 14, 2017, now Pat. No. 10,293,167.

(60) Provisional application No. 62/323,560, filed on Apr. 15, 2016.

(56) References Cited

U.S. PATENT DOCUMENTS

| | | | |
|---|---|---|---|
| 5,978,710 A | 11/1999 | Prutchi et al. | |
| 6,937,906 B2 | 8/2005 | Terry et al. | |
| 7,039,810 B1 | 5/2006 | Nichols | |
| 7,050,855 B2 | 5/2006 | Zeijlemaker et al. | |
| 7,076,283 B2 | 7/2006 | Cho et al. | |
| 7,212,863 B2 | 5/2007 | Strandberg | |
| 7,561,915 B1 | 7/2009 | Cooke et al. | |
| 7,623,930 B2 | 11/2009 | Zeijiemaker et al. | |
| 7,697,988 B2 | 4/2010 | Clement et al. | |
| 8,014,867 B2 | 9/2011 | Cooke et al. | |
| 8,046,063 B2 | 10/2011 | Betzold | |
| 8,121,678 B2 | 2/2012 | Linder et al. | |
| 8,200,334 B1 | 6/2012 | Min et al. | |
| 8,433,408 B2 | 4/2013 | Ellilgson et al. | |
| 8,437,862 B2 | 5/2013 | Yoon et al. | |
| 8,467,882 B2 | 6/2013 | Ellingson et al. | |
| 8,538,550 B2 | 9/2013 | Stubbs et al. | |
| 8,554,318 B2 | 10/2013 | Legay | |
| 8,737,862 B2 | 5/2014 | Manico et al. | |
| 8,744,578 B2 | 6/2014 | Ellingson | |
| 8,805,496 B2 | 8/2014 | Ellingson | |
| 8,818,506 B2 | 8/2014 | Legay | |
| 8,886,317 B2 | 11/2014 | Cooke et al. | |
| 8,896,462 B2 | 11/2014 | Skoldengen et al. | |
| 8,929,995 B2 | 1/2015 | Stancer et al. | |
| 9,008,788 B2 | 4/2015 | Jenison | |
| 9,095,721 B2 | 8/2015 | Stancer et al. | |
| 9,138,584 B2 | 9/2015 | Stancer et al. | |
| 9,174,058 B2 | 11/2015 | Ellingson et al. | |
| 9,272,152 B2 | 3/2016 | Lalonde et al. | |
| 9,919,158 B2 | 3/2018 | Ellingson et al. | |
| 10,130,282 B2 | 11/2018 | Goetz et al. | |
| 10,130,822 B2 | 11/2018 | Legay et al. | |
| 10,293,167 B2 * | 5/2019 | Yoon | A61N 1/3718 |
| 10,441,798 B2 | 10/2019 | Yoon et al. | |
| 10,493,286 B2 | 12/2019 | Ellingson et al. | |
| 10,668,292 B2 | 6/2020 | Pei et al. | |
| 10,744,320 B2 | 8/2020 | Newman et al. | |
| 10,981,010 B2 | 4/2021 | Yoon et al. | |
| 11,253,707 B2 | 2/2022 | Yoon et al. | |
| 11,478,647 B2 | 10/2022 | Ellingson et al. | |
| 11,724,111 B2 * | 8/2023 | Yoon | A61N 1/3931 |
| | | | 607/4 |
| 11,938,326 B2 | 3/2024 | Yoon et al. | |
| 2003/0144705 A1 | 7/2003 | Funke | |
| 2003/0144706 A1 | 7/2003 | Funke | |
| 2004/0024421 A1 | 2/2004 | Ideker et al. | |
| 2004/0030256 A1 * | 2/2004 | Lin | A61B 5/349 |
| | | | 600/509 |
| 2004/0254614 A1 | 12/2004 | Spinelli et al. | |
| 2005/0096708 A1 | 5/2005 | Seim et al. | |
| 2005/0149126 A1 | 7/2005 | Libbus | |
| 2006/0167496 A1 | 7/2006 | Nelson et al. | |
| 2006/0293591 A1 | 12/2006 | Wahlstrand et al. | |
| 2007/0265662 A1 | 11/2007 | Ufford | |
| 2008/0154342 A1 | 6/2008 | Digby et al. | |
| 2009/0157146 A1 | 6/2009 | Linder et al. | |
| 2010/0137945 A1 | 6/2010 | Gadagkar et al. | |
| 2011/0077706 A1 * | 3/2011 | Ellingson | A61N 1/3718 |
| | | | 607/59 |
| 2011/0093046 A1 | 4/2011 | Ellingson et al. | |
| 2011/0106204 A1 | 5/2011 | Yoon et al. | |
| 2011/0152672 A1 | 6/2011 | Doerr et al. | |
| 2011/0160565 A1 | 6/2011 | Stubbs et al. | |
| 2011/0160791 A1 | 6/2011 | Ellingson et al. | |
| 2011/0187360 A1 | 8/2011 | Maile et al. | |
| 2011/0196450 A1 | 8/2011 | McClure | |
| 2012/0221068 A1 | 8/2012 | Ellingson | |
| 2012/0245452 A1 | 9/2012 | Doerr et al. | |
| 2012/0277817 A1 | 11/2012 | Ellingson et al. | |
| 2013/0268012 A1 | 10/2013 | Sison | |
| 2013/0289384 A1 | 10/2013 | Jenison et al. | |
| 2014/0100624 A1 | 4/2014 | Ellingson | |
| 2016/0015986 A1 | 1/2016 | Seeberger et al. | |
| 2016/0151623 A1 | 6/2016 | Doerr | |
| 2016/0151624 A1 | 6/2016 | Doerr | |
| 2017/0296827 A1 | 10/2017 | Yoon et al. | |
| 2017/0296835 A1 | 10/2017 | Yoon et al. | |
| 2018/0140856 A1 | 5/2018 | Lindevig et al. | |
| 2020/0230423 A1 | 7/2020 | Chen et al. | |
| 2023/0027466 A1 | 1/2023 | Ellingson et al. | |
| 2023/0061204 A1 | 3/2023 | Edmonson et al. | |
| 2023/0181912 A1 | 6/2023 | Edmonson et al. | |
| 2024/0207620 A1 | 6/2024 | Yoon et al. | |

OTHER PUBLICATIONS

Kloostermann, Dr. E. Martin, MRI Remote Control Study (ROCON). Remote Management of Cardiac Devices Undergoing MRI, received Mar. 3, 2016, 30 pgs.

Kloostermann, Dr. E. Martin,, "Novel MRI Safe Mode Selection Algorithm Standardized Real-Time Solutions for a Varialbe Time-Dependent Problem", J. Clin Exp. Cardiology, Dec. 11-12, 2017, 22nd World Cardiology Conference.

Prosecution History from U.S. Appl. No. 15/487,713, now issued U.S. Pat. No. 10,293,167, dated May 11, 2018 through Jan. 9, 2019, 62 pp.

Prosecution History from U.S. Appl. No. 16/409,921, now issued U.S. Pat. No. 10,981,010, dated Dec. 10, 2020 through Dec. 23, 2020, 19 pp.

Prosecution History from U.S. Appl. No. 17/234,746, now issued U.S. Pat. No. 11,724,111, dated Feb. 23, 2022 through Jun. 27, 2023, 56 pp.

* cited by examiner

METHODS AND IMPLANTABLE MEDICAL SYSTEMS THAT IMPLEMENT EXPOSURE MODES OF THERAPY THAT ALLOW FOR CONTINUED OPERATION DURING EXPOSURE TO A MAGNETIC DISTURBANCE

CROSS REFERENCE TO RELATED APPLICATIONS

This application is a Continuation application of U.S. patent application Ser. No. 17/234,746, filed Apr. 19, 2021, entitled "METHODS AND IMPLANTABLE MEDICAL SYSTEMS THAT IMPLEMENT EXPOSURE MODES OF THERAPY THAT ALLOW FOR CONTINUED OPERATION DURING EXPOSURE TO A MAGNETIC DISTURBANCE," which is a Continuation application of U.S. patent application Ser. No. 16/409,921, filed May 13, 2019, entitled "METHODS AND IMPLANTABLE MEDICAL SYSTEMS THAT IMPLEMENT EXPOSURE MODES OF THERAPY THAT ALLOW FOR CONTINUED OPERATION DURING EXPOSURE TO A MAGNETIC DISTURBANCE," which is a Divisional application of U.S. patent application Ser. No. 15/487,713, filed Apr. 14, 2017, entitled "METHODS AND IMPLANTABLE MEDICAL SYSTEMS THAT IMPLEMENT EXPOSURE MODES OF THERAPY THAT ALLOW FOR CONTINUED OPERATION DURING EXPOSURE TO A MAGNETIC DISTURBANCE," which claims the benefit of the filing date of provisional U.S. Patent Application No. 62/323,560, filed Apr. 15, 2016, entitled "METHODS AND IMPLANTABLE MEDICAL SYSTEMS THAT IMPLEMENT EXPOSURE MODES OF THERAPY THAT ALLOW FOR CONTINUED OPERATION DURING EXPOSURE TO A MAGNETIC DISTURBANCE," the content of both of which is incorporated by reference in their entirety.

TECHNICAL FIELD

Embodiments relate to implantable medical devices that provide modes of therapy such as providing cardiac pacing. More specifically, embodiments relate to implantable medical systems that allow for an exposure mode of therapy to be controlled to allow for continued operation during exposure to a magnetic disturbance like that created by a magnetic resonance imaging (MRI) scan or other medical procedures.

BACKGROUND

Implantable medical devices may perform various functions in order to deliver modes of therapy to a patient. For example, cardiac stimulation devices like pacemakers and defibrillators may sense electrical physiologic signals in some modes of therapy in addition to providing electrical pacing signals to one or more chambers of the heart. Some modes of therapy that sense a physiologic signal then use that signal when determining how to control the pacing signal.

Patients that have an implantable medical device may be exposed to magnetic disturbances like those caused by MRI scans or other medical procedures. These magnetic disturbances may result in the device sensing signals that are not actually physiologic but are artificially created by the magnetic disturbances. If the device is allowed to control the pacing signal based on the sensed artificial signal, then the pacing signal may be inappropriate or even harmful for the patient. Therefore, it is commonplace to utilize an exposure mode of therapy during such disturbances where the exposure mode deactivates sensing or otherwise ignores the sensed signal and paces asynchronously in a pre-defined pacing configuration with a pre-defined pacing rate. This may not be an optimal exposure mode of therapy, especially for certain patients having particular device types such as those with pacing ability but being primarily for defibrillation purposes. Likewise, the pre-defined pacing rate may not be an optimal rate of pacing for patients with other pacing needs.

SUMMARY

Embodiments address issues such as these and others by applying various considerations in order to determine an appropriate mode of therapy and/or an appropriate rate when the device is in an exposure mode such as during times when a magnetic disturbance is present. For instance, the type of device may be considered to determine whether a pace capable device is primarily for pacing only or for defibrillation or for cardiac resynchronization with defibrillation abilities. A measure of the prior rate of cardiac activity, such as an average of a prior intrinsic rate or of a prior pacing rate, may be factored into the determination of an appropriate asynchronous rate. Additionally, the device may continue to sense the intrinsic rate and then analyze that intrinsic rate to determine whether the intrinsic rate is physiologic or artificial. The pacing mode may then be set to use a physiologic intrinsic rate to trigger the pacing signal or to use the asynchronous pacing rate and ignore an artificial intrinsic rate.

Embodiments provide a method of controlling an exposure mode of therapy of an implantable medical device. The method involves determining a device type of the implantable medical device. Upon detecting a need to switch to the exposure mode, the method further involves selecting the exposure mode of therapy of the implantable medical device based on the device type and a pre-exposure mode of therapy. The method then involves implementing the exposure mode of operation at the implantable medical device.

Embodiments provide a method of controlling an exposure mode of therapy of an implantable medical device. After detecting the need to switch to the exposure mode, the method involves sensing an intrinsic rate of cardiac activity and comparing the intrinsic rate to at least one reference value to determine if the intrinsic rate is physiologic or artificial. When the intrinsic rate is physiologic, then the method further involves implementing the exposure mode of therapy that includes sensing and using triggered pacing. When the intrinsic rate is artificial, then the method further involves implementing the exposure mode of therapy that includes asynchronous pacing.

Embodiments provide an implantable medical system that includes a device for providing electrical sensing and pacing. The device further includes a controller that is in control of the device to provide an exposure mode of therapy by the device. The controller is configured to determine a device type, detect a need to switch to the exposure mode, select the exposure mode of therapy of the device based on the device type and a pre-exposure mode of therapy, and implement the exposure mode of operation at the device.

Embodiments provide an implantable medical system that includes a device for providing electrical sensing and pacing. The implantable medical system further includes a controller that is in control of the device to provide an exposure mode of therapy by the device. The controller is configured to sense an intrinsic rate of cardiac activity after detecting a need to switch to the exposure mode, compare the intrinsic rate to at least one reference value to determine if the intrinsic rate is physiologic or artificial, when the intrinsic rate is physiologic then implement the exposure mode of therapy that includes sensing and using triggered pacing, and when the intrinsic rate is artificial then implement the exposure mode of therapy that includes asynchronous pacing.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Embodiments provide an implantable medical system that employs various considerations to determine an appropriate exposure mode of therapy such as during times when the system is exposed to a magnetic disturbance. Considerations may include the type of implantable medical device that is present in the system and the manner of use of the device in pre-exposure modes. Considerations may also include whether a sensed intrinsic signal is physiologic and therefore reliable for triggering pacing or artificial and therefore unreliable. Considerations may further include pre-exposure mode rates.

Figure 1:
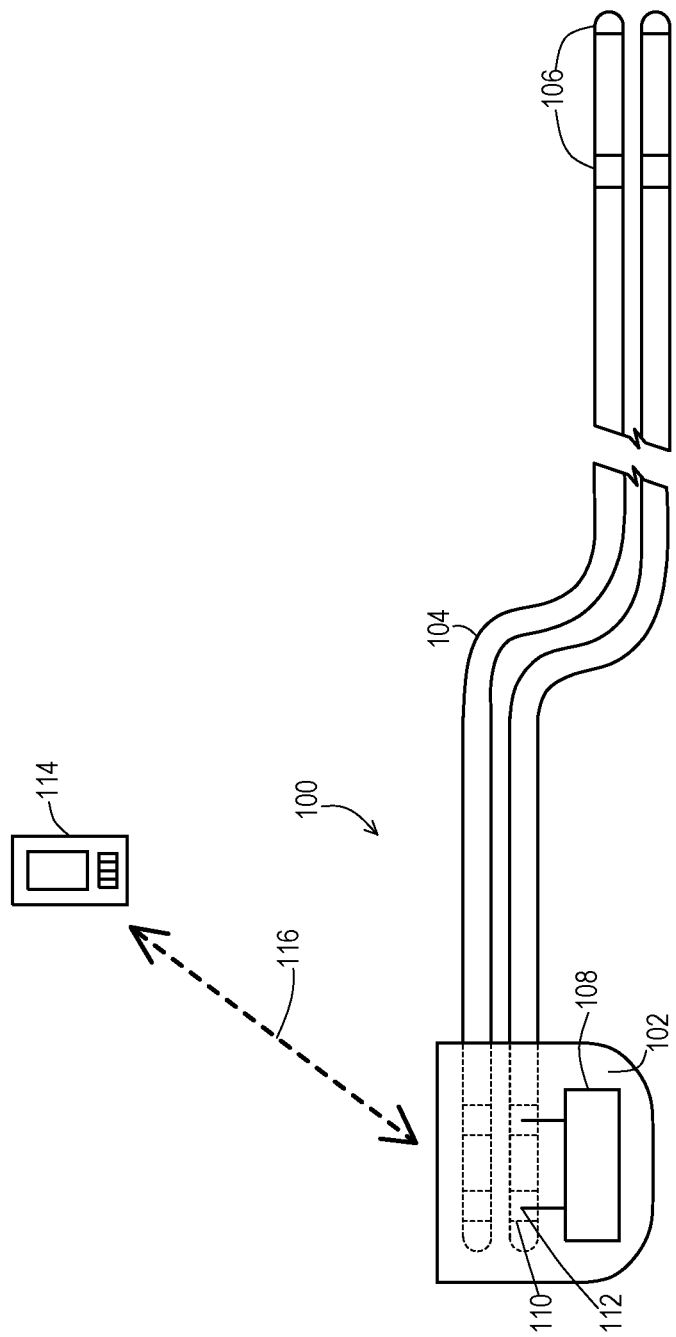
FIG. 1 shows an example of an implantable medical system that may operate according to various embodiments disclosed herein.

FIG. 1 shows an example of an implantable medical system according to embodiments disclosed herein. A patient receives an implantable medical system 100 which, in this example, implantable medical system 100 includes an implantable medical device 102 that has the ability to perform electrical sensing and pacing. The implantable medical device (IMD) 102 may be of various types and some of those types may offer additional functionality such as defibrillation and/or cardiac resynchronization therapy. The IMD 102 may even be primarily for non-pacing functions like defibrillation and/or cardiac resynchronization although may include the ability to pace if needed. A collection 108 of electrical components is included to provide these functions.

The implantable medical system 100 in some cases may also include one or more electrical leads 104. The electrical lead(s) 104 are electrically connected to the IMD 102 via proximal contacts 110 on the leads 104 and electrical connectors 112 of the IMD 102. The leads 104 include electrodes 106 on a distal end that interface with the body tissue to capture electrical physiologic signals or deliver electrical pacing signals.

The implantable medical system 100 in some cases may omit the use of electrical leads 104. In this embodiment, electrodes 106 integrated into the TMID 102 that interface with the body tissue to capture electrical physiologic signals or deliver electrical pacing signals.

Additionally, in some cases the implantable medical system 100 may include external devices 114 such as hand-held controllers that are capable of communicating wirelessly with the IMD 102. The wireless communications 116 may be near field, arm's length, far field and the like as is known in the art. The external device 114 may generate commands to the IMD 102 to request information about the IMD 102 and/or to instruct the IMD 102 to operate in a particular way. In particular, in some cases the external device 114 may be used to manually switch the IMD 102 to enter an exposure mode of therapy. Alternatively or additionally, the IMD 102 may have the ability to automatically detect magnetic disturbances and then automatically enter an exposure mode of therapy.

Figure 2:
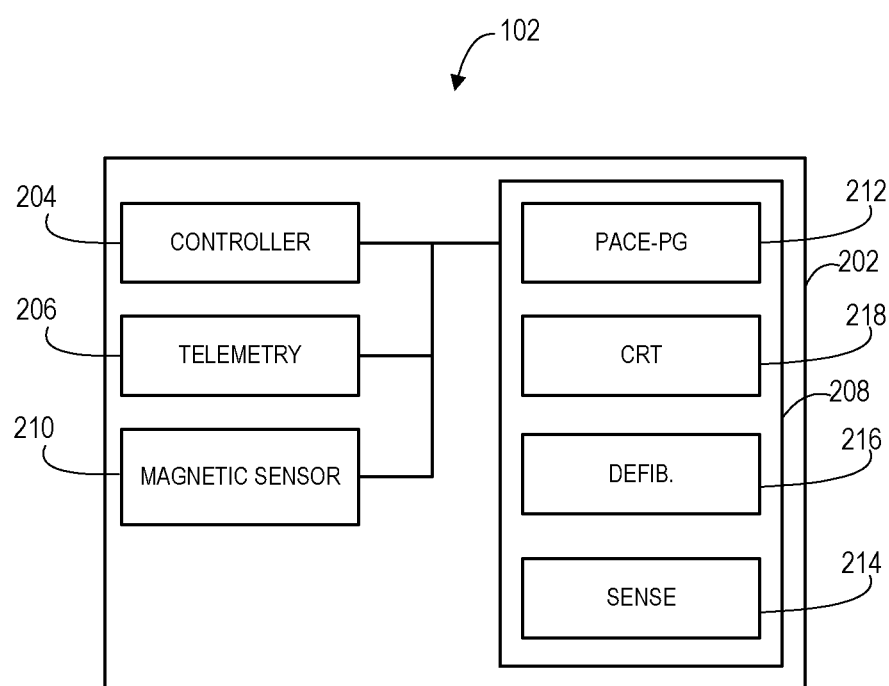
FIG. 2 shows an example of components of the implantable medical system.

FIG. 2 shows an example of components of an IMD 102. The IMD 102 may include a housing 202 that contains the various components. The IMD 102 includes a controller 204 that may control the operations of the IMD 102 by communicating with other components. The controller 204 may be of various forms such as a general purpose programmable processor, a dedicated purpose processor, hardwired digital logic, and the like. The controller may also include internal or external memory having computer-readable instructions that, when executed by controller 204 cause controller 204 to perform various operations attributed to it in this disclosure. The memory may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

The IMD 102 may include telemetry 206 to communicate wireless with external devices such as the external device 114. As discussed above, the IMD 102 may communicate via one or more types of wireless communications including near field, arm's length, far field and the like. For instance, the telemetry 206 may include inductive coupling for near field or arm's length, may include radio frequency far field functions such as those operating in the Medical Implant Communication Service (MICS) band.

The IMD 102 also includes a therapy device 208 that may include one or more engines for providing various therapy functions. For instance, the therapy device 208 may include a configurable pacing engine 212 that may pace one or more chambers of the heart via corresponding one or more electrodes of the lead 104. The therapy device 208 may include a configurable sensing engine 214 to sense from one or more chambers of the heart. Likewise, depending upon the type of IMD 102, the therapy device 208 may include a defibrillation engine 216 capable of providing high voltage defibrillation shocks. Again depending upon the type of IMD 102, the therapy device 208 may include a cardiac resynchronization engine 218 capable of provide cardiac resynchronization signals. In some embodiments a single "engine" may be used for multiple types of therapy, such as a single pacing engine that provides bradycardia pacing, anti-tachycardia pacing and/or cardiac resynchronization pacing therapy.

The engine(s) may be implanted in the form of one or more modules. For instance, a therapy delivery module may provide the pacing, resynchronization, or/and defibrillation functions. In one example, an engine may include a low voltage (LV) therapy module for delivering low voltage pacing pulses using an extra-cardiovascular pacing electrode vector selected from various electrodes. LV therapy module may be configured to deliver low voltage pacing pulses, e.g., 8 V or less or 10 V or less. One or more capacitors included in the LV therapy module are charged to a voltage according to a programmed pacing pulse amplitude by a LV charging circuit, which may include a state machine. The LV charging circuit may charge the capacitors to a multiple of the voltage of a battery included in a power source without requiring a transformer. At an appropriate time, the LV therapy module couples the capacitor(s) to a pacing electrode vector to deliver a pacing pulse to the heart.

An engine may additionally or alternatively include a high voltage (HV) therapy module that includes one or more high voltage capacitors. When a shockable rhythm is detected, the HV capacitor(s) is(are) charged to a shock voltage amplitude by a HV charging circuit according to the programmed shock energy. The HV charging circuit may include a transformer and be a processor-controlled charging circuit that is controlled by a control module. The control module applies a signal to trigger discharge of the HV capacitor(s) upon detecting a feedback signal from therapy delivery module that the HV capacitors have reached the shock voltage amplitude required to deliver the programmed shock energy. In this way, control module controls operation of the high voltage therapy module to deliver CV/DF shocks using defibrillation electrodes and/or a device housing.

HV therapy module may be used to deliver cardiac pacing pulses. In this case, the HV capacitor(s) is(are) charged to a much lower voltage than that used for delivering shock therapies but may be higher than the maximum available pulse voltage amplitude produced by the LV therapy module. For example, the HV capacitor may be charged to 40 V or less, 30 V or less, or 20 V or less for producing extra-cardiovascular pacing pulses.

Compared to pacing pulses delivered by LV therapy module, pulses delivered by HV therapy module may have a higher voltage amplitude and relatively longer pulse width for delivering higher energy pacing pulses for capturing the heart. More current may be delivered using a low impedance pacing electrode vector. Longer pulse width is attainable due to a higher capacitance (and consequently higher RC time constant) of the HV capacitor(s). The LV therapy module may be capable of producing a maximum pulse voltage amplitude of up to and including 10 V. The maximum single-pulse pacing pulse width produced by LV therapy module may be 2 ms. In some examples, LV therapy module may be configured to produce composite pacing pulses comprising two or more individual pulses fused in time to deliver a cumulative composite pacing pulse energy that captures the heart. Techniques for delivering composite pacing pulses are generally disclosed in the U.S. patent application Ser. No. 15/367,516 and in provisional U.S. Pat. Application No. 62/262,412 and corresponding pending U.S. patent application Ser. No. 15/368,197, all of which are incorporated herein by reference in their entirety. The maximum composite pacing pulse width may be up to 8 ms or higher.

Additionally, the IMD 102 may include one or more sensors 210 for detecting magnetic disturbances. For instance, Hall effect sensors may be used to detect that a magnetic field of a particular intensity is present. This allows the controller 204 to then enter an exposure mode. The controller 204 may then distinguish whether the magnetic field is representative of a programming trigger caused by a programming magnet being placed near the site of implantation of the IMD 102 or is a magnetic disturbance like that from an MRI machine or other source that necessitates an exposure mode of therapy. For instance, the controller 204 may utilize various techniques to distinguish the programming magnet from an MRI machine. Examples include determining magnetic field strength particularly at multiple locations, determining force resulting from the magnetic field, determining torque resulting from the magnetic field, determining magnetic field direction particularly as measured at multiple locations, and the like to then determine if threshold are met that are indicative of a magnetic field from an MRI machine. Examples of such techniques are disclosed in U.S. application Ser. Nos. 13/046,158; 13/456,891; 13/587,368; and Ser. No. 14/340,893, all of which are incorporated by reference herein in their entirety.

Figure 3:
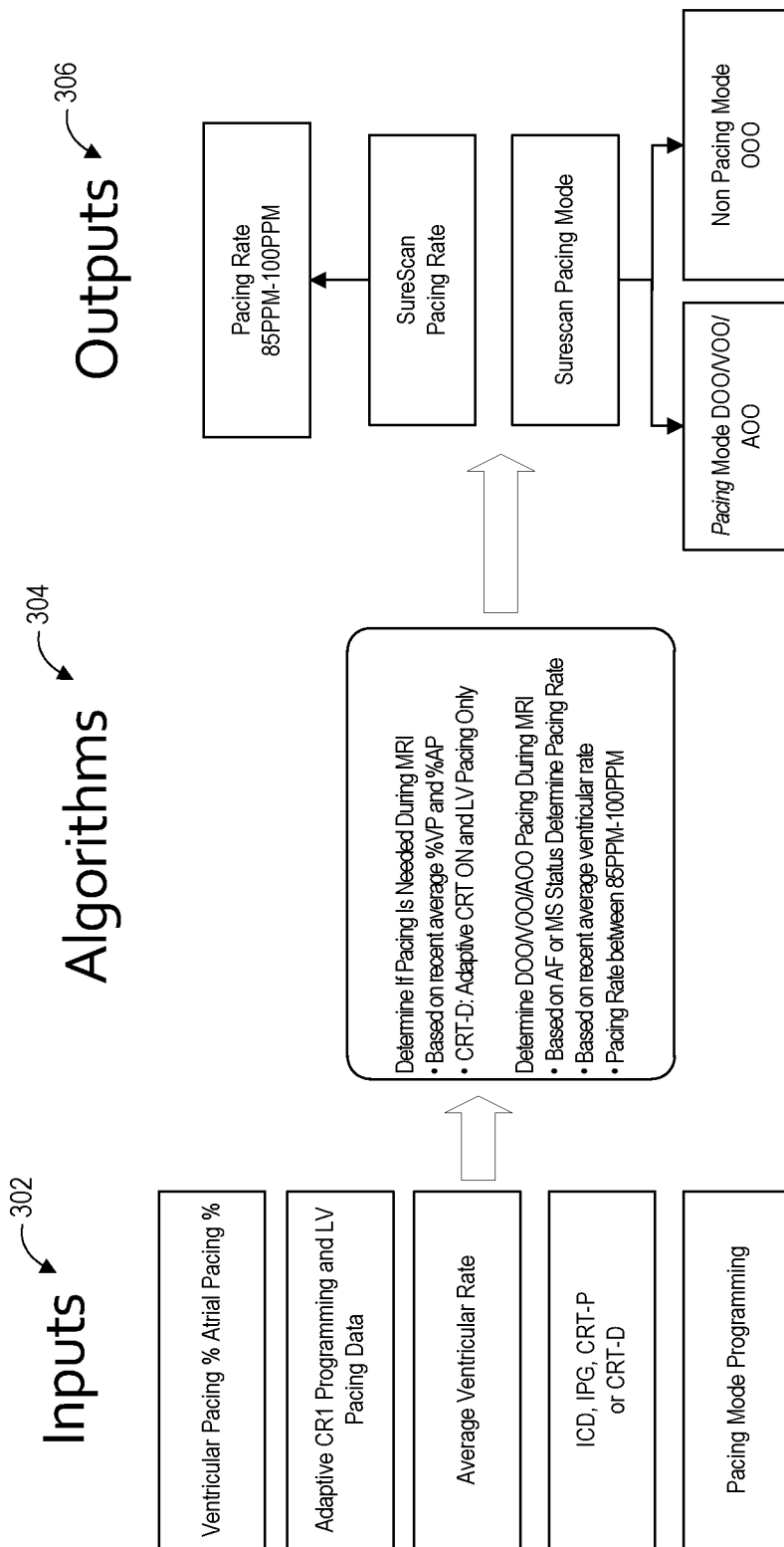
FIG. 3 shows an example of inputs, considerations, and resulting output decisions when implementing an exposure mode of operation at the implantable medical system.

FIG. 3 shows a basic flow of information that may be used by a controller, such as a controller within the external device 114 or the internal controller 204 of the IMD 102, to make a determination as to the appropriate exposure mode and rate of therapy that should be employed. This basic flow of information may be used to invoke the appropriate exposure mode once it has been detected, either by manual programming or by automatic detection, that the IMD 102 should switch to the exposure mode. The controller may gather information to be used as inputs 302. Examples of the inputs include various pieces of information from the pre-exposure mode operation such as: pacing percentage for both ventricular and atrial pacing; adaptive and/or general cardiac resynchronization therapy programming including which ventricles are being stimulated; the average ventricular rate of pacing; the type of device including whether the device is an implantable cardiac defibrillator (ICD), an implantable pulse generator (IPG) primarily for pacing, a cardiac resynchronization therapy (CRT) device with pacing ability but not defibrillation, or a CRT device that also includes defibrillation ability; and pacing mode programming including which chambers are being paced.

The controller may then process this input information 302 via considerations 304. For instance, the controller may determine whether pacing is even needed during the period of time that exposure mode is active, such as during an MRI scan. Factors include what the prior pacing percentage is and in the case of CRT, whether the cardiac resynchronization stimulation is only being applied to the left ventricle or to other chambers.

The considerations 304 may also include determining what the pacing mode should be if pacing is needed, such as whether to pace the atrium, ventricle, or both. This may be based on the pre-exposure programming as well as current status such as whether atrial fibrillation is occurring and whether a mode switch due to atrial fibrillation is warranted to avoid wasting atrial pacing signals.

The considerations 304 may also include determining the pacing rate. For using asynchronous mode of pacing, the fixed rate may be based on a pre-exposure mode factor such as the average ventricular rate. Furthermore, consideration may be given to a pre-defined range of rates. For instance, for a given patient, it may be desirable to contain the fixed rate to somewhere between 85 and 100 paces per minute. As discussed below in reference to FIG. 5, in some embodiments it may be desirable to also consider whether it is possible to sense an intrinsic rate that is physiologic rather than artificial while in the exposure mode and in that case trigger pacing from the intrinsic rate rather than using asynchronous pacing at the previously established asynchronous rate. The result of these considerations 304 is to produce outputs 306 necessary to implement the particular exposure pacing mode rate.

Figure 4:
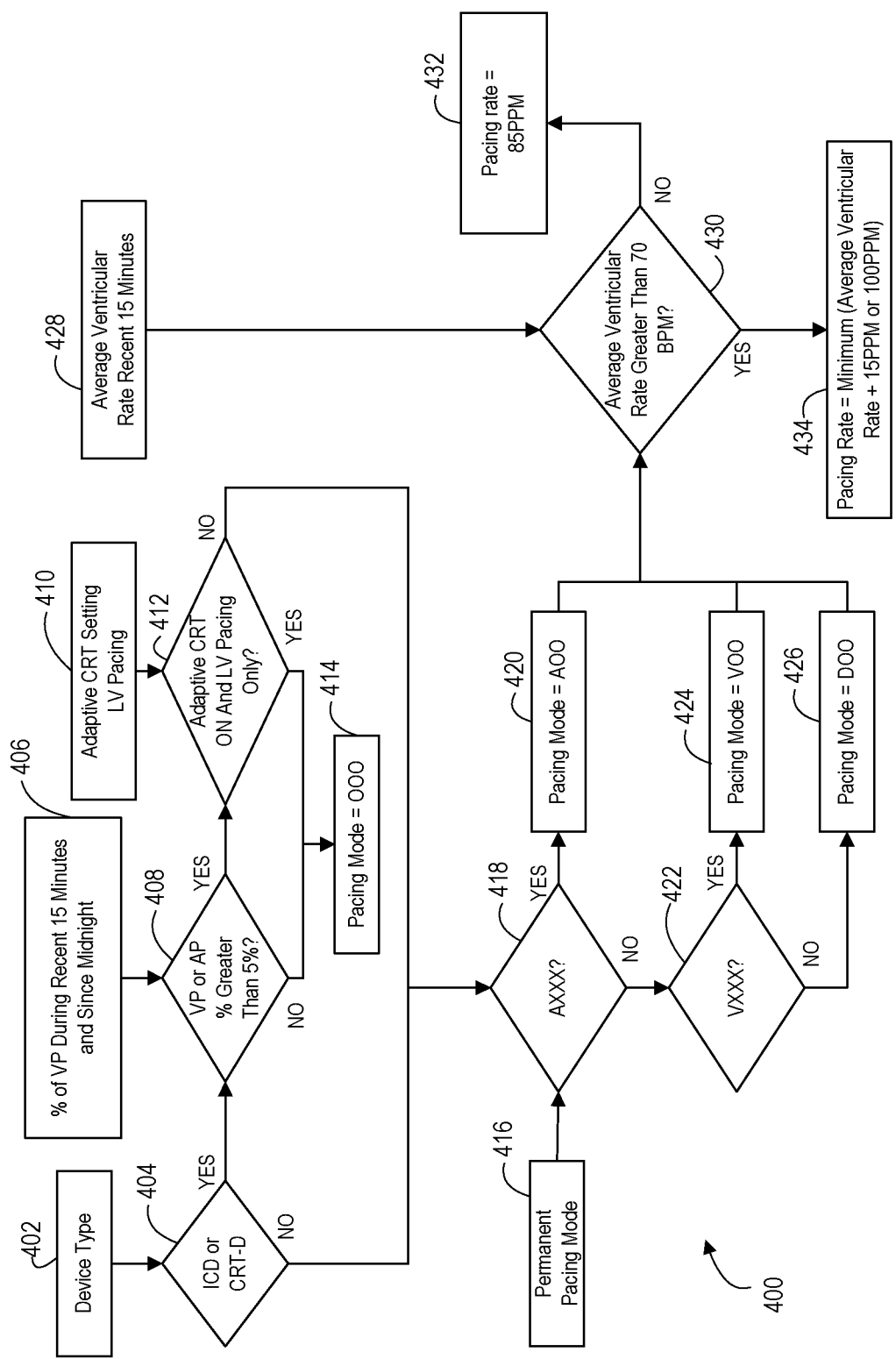
FIG. 4 shows an example of logical operations that may be performed by the implantable medical system to consider device type and prior rate of cardiac activity when establishing the exposure mode of therapy.

FIG. 4 shows an example 400 of logical operations that a controller may employ to ultimately select the pacing mode and rate for the exposure mode of therapy. Initially, the type of IMD 102 is determined at a query 404 that accesses the device type information 402. For instance, where the controller performing these operations is the external device 114 being used to manually program the IMD 102 to enter the exposure mode, the external device 114 may send a wireless request for information at the query 404 to obtain the device type 402 from the IMD 102. Where the controller 202 of the IMD 102 is the controller performing these operations either in response to a command from the external device 114 to enter the exposure mode or where the IMD 102 has detected the magnetic disturbance and has automatically entered the exposure mode, then the controller 202 accesses the locally stored device type information 402.

Regardless of which device performs these operations, query operation 404 determines from the device type information 402 whether the IMD 102, and specifically the therapy device 208, is of the type that can provide defibrillation. For instance, query operation 404 may specifically check for an ICD or a CRT device with defibrillation. Operational flow then proceeds to a query operation 408 when the IMD 102 does have defibrillation ability or proceeds to query operation 418 when the IMD 102 does not have defibrillation ability.

It is also to be appreciated that an external device 114 may implement the query 404 and then provide the IMD 102 with instruction regarding whether the controller 204 should then proceed with the remainder of these operations by beginning at the query operation 408 or at the query operation 418. The controller 204 may then proceed with the remainder of these operations where the controller 204 then utilizes pre-exposure mode information without being required to uplink that information to the external device 114. However, where the external device 114 performs all of these operations or where the query 404 is based to some degree on pre-exposure mode programming (e.g., CRT-D with defibrillation deactivated to behave as a CRT-P), then the pre-exposure mode information is uplinked from the IMD 102 to the external device 114 and the external device 114 downlinks the instruction for the proper exposure mode and rate.

It is also to be noted that at query operation 404, it is possible in some embodiments that no pre-exposure mode information has been needed because the type of device is entirely hardware based and not affected by pre-exposure programming. In that case an IMD 102 that has the ability to automatically enter the exposure mode may be programmed by the manufacturer regarding which branch of logic to use in FIG. 4 that stems from the query operation 404. In that case, the initial programming being loaded onto the IMD 102 from the manufacturer utilizes the device type information 402 to specify in the initial programming which query operation should be the first operation to be performed by the IMD 102 upon automatically entering exposure mode, either query operation 408 or query operation 418. In that case, the IMD 102 need not perform the query operation 404 upon entering the exposure mode since that query 404 was already resolved at the time of initial programming.

In any of these alternatives above, operational flow proceeds to query 408 where the device type is such that defibrillation is available and proceeds to the query operation 418 otherwise. For device types leading to the query operation 408, the controller determines from pacing percentage information 406 stored by the IMD 102 whether the pacing percentage (considering either atrial or ventricular) is greater than a threshold. The pacing percentage information 406 may be based on pacing activity for some pre-exposure period immediately preceding the exposure mode, such as 15 minutes or for the entire day such as since midnight. For example, query 408 may determine whether the IMD 102 has been pacing the ventricle more than 5% of the pacing cycles for the 15 minutes preceding the exposure mode. It will be appreciated that other pacing percentage thresholds may also be applied but 5% is believed to be effective for most patients. If the pacing percentage is lower than the threshold, this indicates that it is appropriate for the patient to go without pacing for a short time such as for the duration of an MRI scan, and in that case the controller selects that there be no pacing via pacing mode OOO for the exposure mode as indicated at pacing state 414. While pacing state 414 shows the pacing mode as OOO, it will be appreciated that this is just one example of the OXO modes that may be used.

If the pacing percentage is at the query operation 408 is greater than the pacing threshold, then the controller determines at a query operation 412 whether the device is performing adaptive and/or general CRT with left ventricle pacing only by referencing the pre-exposure mode information 410. If CRT is being used with only left ventricle pacing, then even though the pacing percentage is above the threshold, it is still appropriate to stop the left ventricle pacing for a short period of time and the controller selects that there be no pacing for the exposure mode as pacing mode OOO as indicated at pacing state 414.

If the controller finds that CRT is being used and more than merely left ventricle pacing is occurring, then the controller concludes that some form of pacing is needed. Therefore, the controller then proceeds to the query operation 418 just as if query operation 404 had not found that the device was defibrillation capable (i.e., that the IMD 102 is a type that is primarily for pacing instead of primarily for defibrillation).

At the sequence of query operations 418 and 422, the controller then determines what the pre-exposure pacing mode has been by referencing the pre-exposure mode pacing mode information 416. This pre-exposure pacing mode, also referred to as the permanent pacing mode, is AXX, VXX, or DXX. The controller sets the exposure mode to pace the same set of chambers as the pre-exposure mode, so where the pre-exposure pacing mode is AXX, then in this embodiment the controller selects that there be atrial pacing for the exposure mode by using asynchronous pacing mode AOO as indicated at pacing state 420. Where the pre-exposure pacing mode is VXX, then in this embodiment the controller selects that there be ventricular pacing for the exposure mode by using asynchronous pacing mode VOO as indicated at pacing state 424. Where the pre-exposure pacing mode is DXX, then in this embodiment the controller selects that there be dual chamber pacing for the exposure mode by using asynchronous pacing mode DOO as indicated at pacing state 426.

Once the pacing mode for the exposure mode has been set, the controller then proceeds to a query operation 430 to determine an appropriate exposure mode pacing rate for the chosen pacing mode. The query operation 430 determines whether a pre-exposure mode rate of cardiac activity as specified in pre-exposure mode information 428 exceeds a rate threshold. The pre-exposure mode information 428 may be one of various different pieces of information. For example, the pre-exposure mode information 428 may specify an average ventricular rate taken over a 15 minute period immediately preceding the exposure mode. This pre-exposure mode average rate may be an average intrinsic rate that has been sensed or it may be an average paced rate.

It will be appreciated that the rate threshold applied at the query operation 430 may vary but it has been found that 70 beats per minute is an effective example. If the threshold is not exceeded by the pre-exposure mode rate, then the controller sets the asynchronous pacing rate to a pre-defined fixed value such as 85 beats per minute as indicated at the pacing rate state 432. It will be appreciated that this pre-defined fixed value may vary, but 85 beats per minute are known to be acceptable for most patients. If the threshold is exceeded by the pre-exposure mode pacing rate, then the controller sets the asynchronous pacing rate to a fixed value that is equal to the pre-exposure mode rate plus a fixed adjustment but with an upper limit at the pacing rate state 434. For example, the controller may set that asynchronous pacing rate to the pre-exposure rate plus 15 additional paces per minute with an upper limit of 100 paces per minute. The fixed adjustment may vary but it has been found that an adjustment of 15 additional paces per minute adequately avoids a competitive pacing condition. Furthermore, the upper limit may vary but it has been found that an upper limit of 100 paces per minute is adequate. Therefore, in this particular example, the pacing rate for the exposure mode will be set within the range of 85-100 paces per minute.

Figure 5:
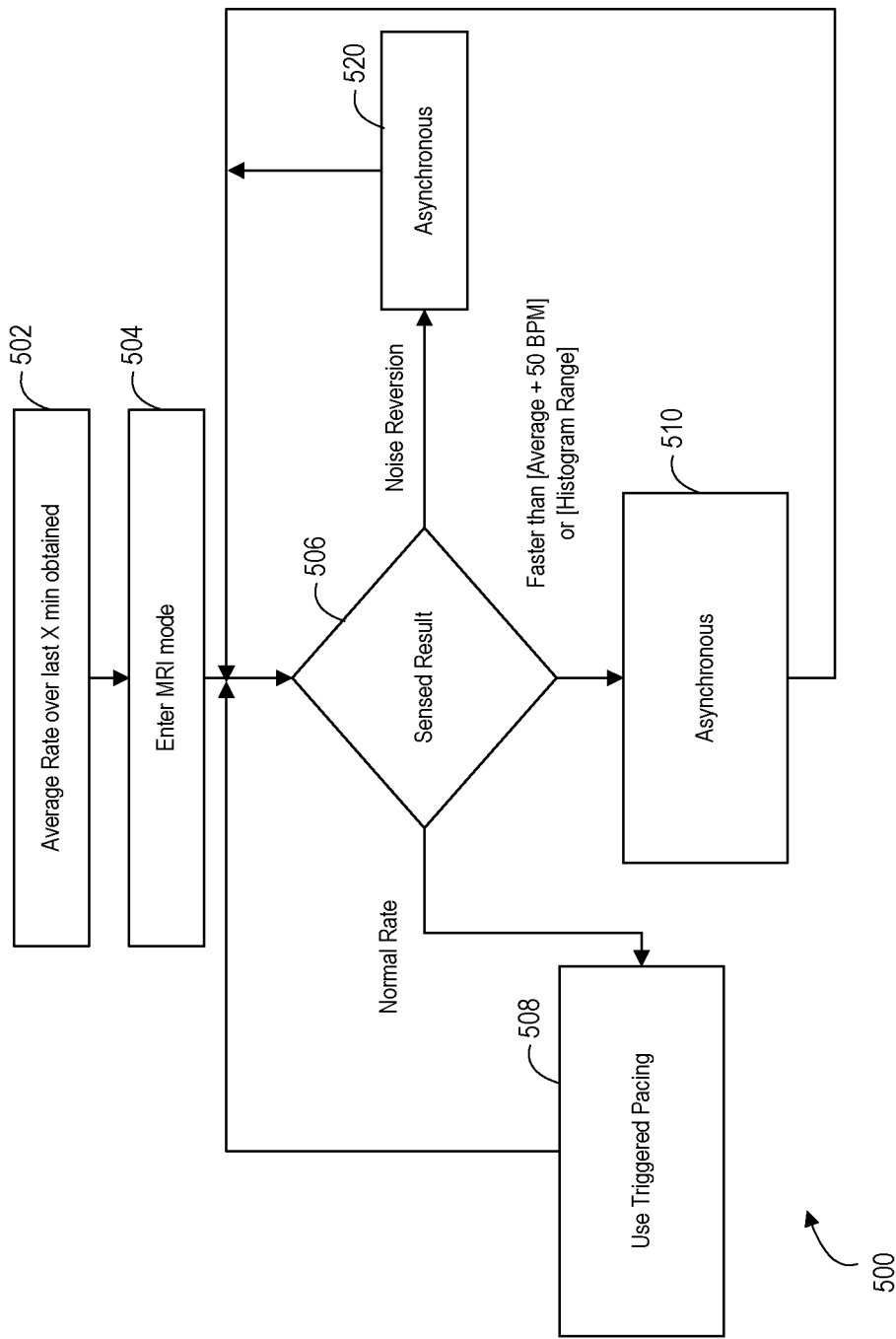
FIG. 5 shows an example of logical operations that may be performed by the implantable medical system to consider whether a sensed intrinsic rate is physiologic or artificial and whether to utilize triggered pacing or asynchronous pacing as the exposure mode of therapy.

FIG. 5 shows an example 500 of logical operations that may be used by the controller 204 to continuously adapt the exposure mode to use a triggered pacing mode when possible and to otherwise use an asynchronous fixed pacing rate. In this example, the average rate, either intrinsic or paced, over some period of time preceding the exposure mode is obtained at the rate operation 502. When needed, the exposure mode, also referred to as the MRI mode, is entered at the operation 504. The controller then begins monitoring the sensing for an intrinsic rate at a query operation 506.

Because a magnetic disturbance may result in sensing an artificial intrinsic rate that is not appropriate for triggering pacing, the controller 204 utilizes logic at the query operation 506 to determine whether the sensed rate is a normal rate, a faster than normal rate, or a noise reversion which occurs where the rate may be within the normal range but an abrupt change within the range is artificial. The controller compares the sensed rate to at least one reference value, as discussed in more detail below, to make the determination.

When the sensed rate is determined to be normal by the controller, then the controller sets the exposure mode to triggered pacing of the chambers that were being paced in the pre-exposure mode as indicated at the triggered pacing state 508. Thus, the triggered pacing mode may be AAT, VVT, or DDT. The normal rate may be confirmed by using a range of rates known to be normal in general as the reference values to compare against the sensed rate. Alternatively, the reference values to compare to the sensed rate may be more specific to this particular patient by establishing an upper limit for the range of normal rates by utilizing the average intrinsic or paced pre-exposure rate plus an adjustment. As another alternative, the normal rate may be established by maintaining a statistical distribution, such as a histogram, of historical pacing/sensing data and choosing the normal range to be those within a particular range of percentiles. Such a histogram or other statistical distribution may instead be used to determine the adjustment to the average pre-exposure rate by choosing a rate in a larger percentile as the upper limit of the normal range. For example, the upper limit to the normal rate may be the average pre-exposure rate plus 50 beats per minute.

Where the controller detects that the sensed rate falls outside of the normal range, then the controller sets the exposure mode to asynchronous fixed rate pacing as indicated at the pacing state 510. This ensures that the sensed rate, which is possibly artificial, does not produce an inappropriate pacing rate.

Where the controller detects that the sensed rate indicates a noise reversion, then the controller sets the exposure mode to asynchronous fixed rate pacing as indicated at the pacing state 520. The controller may detect the noise reversion by comparing a current sensed rate to immediately prior sensed rates collected during a set period of time that precedes the sensing of the current intrinsic rate and looking for abrupt changes to the sensed rate that are artificial rather than physiologic. This may be done by comparing a difference in the current and prior sensed rates to a threshold where the threshold is chosen to distinguish a physiologic change in rate from an artificial one. For example, a near instantaneous change of 50 beats per minute is more likely to be artificial than physiologic.

Thus, using this example of FIG. 5, the IMD 102 may enter an exposure mode and may transition as needed from triggered pacing to asynchronous pacing. It will be appreciated that the example of FIG. 5 may be used in conjunction with the example of FIG. 4 to also control the exposure mode based on device type. For instance, if the IMD 102 is primarily for defibrillation or CRT with defibrillation and the pacing percentage is low, then pacing may be avoided altogether, but when the example of FIG. 4 determines that pacing should be done while in exposure mode, then the example of FIG. 5 may be further employed to transition between triggered pacing and asynchronous pacing based on the results of analyzing the sensed rate.

Additional information related to the pacing mode includes parameters that may remain fixed. A maximum pacing atrial to ventricular pacing (PAV) limit may be set to a fixed value such as 110 ms to minimize the risk of pacing on a T-wave. If the permanent PAV is already less than this value, then PAV interval may not be extended. Right Ventricular (RV) pacing amplitude and width and Right Atrial (RA) pacing amplitude and width may be set to a fixed value to assure a safety pacing margin and pacing support during an MRI scan. LV amplitude may be maintained at an existing programmed setting for amplitude and width because setting a higher amplitude may result in phrenic stimulations that hinder MRI imaging.

While embodiments have been particularly shown and described, it will be understood by those skilled in the art that various other changes in the form and details may be made therein without departing from the spirit and scope of the invention.

What is claimed is:

1. A method of controlling an exposure mode of therapy of an implantable medical device, comprising:
   determining whether a pacing percentage of the device during a period of time prior to implementing the exposure mode exceeds a threshold;
   when the threshold is not exceeded then selecting a non-pacing mode as the exposure mode;
   when the threshold is exceeded by the pacing percentage, then determining whether a pre-exposure mode of the implantable medical device provides cardiac resynchronization therapy by pacing only a left ventricle of a heart;

when the pre-exposure mode does only pace the left ventricle, then selecting the non-pacing mode as the exposure mode;

when the pre-exposure mode does not only pace the left ventricle, then selecting a pacing mode that paces a same set of chambers of the heart as the pre-exposure mode as the exposure mode; and upon detecting a need to switch to the exposure mode, implementing the selected exposure mode of therapy at the implantable medical device, wherein the implementing comprises providing pacing by the implantable medical device according to the selected exposure mode.

2. The method of claim 1, wherein selecting the pacing mode that paces the same set of chambers of the heart as the pre-exposure mode comprises pacing asynchronously.

3. The method of claim 1, wherein upon selecting the pacing mode that paces the same set of chambers of the heart as the pre-exposure mode, then selecting an exposure mode pacing rate based on pre-exposure rates.

4. The method of claim 3, wherein selecting the exposure mode pacing rate based on the pre-exposure rates comprises determining whether an average rate of cardiac activity occurring during a period prior to implementing the exposure mode exceeds a rate threshold, when the average rate does not exceed the threshold then pacing at a pre-defined fixed rate as the exposure mode pacing rate and when the average does exceed the threshold then pacing at a rate equal to the average rate plus a fixed adjustment up to a pre-defined upper limit.

5. The method of claim 4, wherein the pre-exposure rates of cardiac activity are intrinsic rates.

6. The method of claim 4, wherein the pre-exposure rates of cardiac activity are paced rates.

7. An implantable medical system comprising:
a device for providing electrical sensing and pacing; and
a controller that is in control of the device to provide an exposure mode of therapy by the device and that is configured to:
determine whether a pacing percentage during a period of time prior to implementing the exposure mode exceeds a threshold;

when the threshold is not exceeded then select a non-pacing mode as the exposure mode;

when the threshold is exceeded by the pacing percentage, then determine whether a pre-exposure mode of the implantable medical device provides cardiac resynchronization therapy by pacing only a left ventricle of a heart;

when the pre-exposure mode does only pace the left ventricle, then select the non-pacing mode as the exposure mode;

when the pre-exposure mode does not only pace the left ventricle, then select a pacing mode that paces a same set of chambers of the heart as the pre-exposure mode as the exposure mode; and upon detecting a need to switch to the exposure mode, implement the selected exposure mode of therapy at the device, wherein the implementing comprises providing pacing by the device according to the selected exposure mode.

8. The system of claim 7, wherein the controller selecting the pacing mode that paces the same set of chambers of the heart as the pre-exposure mode comprises pacing asynchronously.

9. The system of claim 7, wherein upon selecting the pacing mode that paces the same set of chambers of the heart as the pre-exposure mode, the controller then selects an exposure mode pacing rate based on pre-exposure rates.

10. The system of claim 9, wherein the controller selecting the exposure mode pacing rate based on the pre-exposure rates comprises determining whether an average rate of cardiac activity occurring during a period prior to implementing the exposure mode exceeds a rate threshold, when the average rate does not exceed the threshold then pacing at a pre-defined fixed rate as the exposure mode pacing rate and when the average does exceed the threshold then pacing at a rate equal to the average rate plus a fixed adjustment up to a pre-defined upper limit.

11. The system of claim 10, wherein the pre-exposure rates of cardiac activity are intrinsic rates.

12. The system of claim 10, wherein the pre-exposure rates of cardiac activity are paced rates.

* * * * *